(12) United States Patent
Tresnak et al.

(10) Patent No.: US 7,017,578 B2
(45) Date of Patent: *Mar. 28, 2006

(54) ENDOTRACHEAL TUBE SYSTEM AND METHOD OF USE

(76) Inventors: Rick J. Tresnak, 601 State St., Dysart, IA (US) 52224; Emil J. Tresnak, 432 East St., Apt. C, Grinnell, IA (US) 50112

( * ) Notice: Subject to any disclaimer, the term of this patent is extended or adjusted under 35 U.S.C. 154(b) by 0 days.

This patent is subject to a terminal disclaimer.

(21) Appl. No.: 10/981,036

(22) Filed: Nov. 4, 2004

(65) Prior Publication Data

US 2005/0235997 A1    Oct. 27, 2005

Related U.S. Application Data

(63) Continuation-in-part of application No. 10/829,033, filed on Apr. 21, 2004.

(51) Int. Cl.
*A61M 16/00* (2006.01)
*A62B 7/00* (2006.01)

(52) U.S. Cl. .......................... 128/207.14; 128/200.26; 128/204.18

(58) Field of Classification Search ........... 128/207.14, 128/202.22, 205.13, 203.28, 205.23, 202.27, 128/200.26, 203.11, 205.24, 207.16, 204.28, 128/205.17

See application file for complete search history.

(56) References Cited

U.S. PATENT DOCUMENTS

| | | | |
|---|---|---|---|
| 2,270,025 A | 1/1942 | Ruhoff | |
| 2,567,445 A | 9/1951 | Parker | |
| 2,785,057 A | 3/1957 | Schwab | |
| 2,880,072 A | 3/1959 | Grosskopf | |
| 2,918,893 A | 12/1959 | Norton | |
| 3,067,015 A | 12/1962 | Lawdermilt | |
| 3,068,073 A | 12/1962 | Stanford | |
| 3,373,735 A * | 3/1968 | Gallagher | 600/581 |
| 3,420,635 A | 1/1969 | Davis | |
| 3,754,867 A | 8/1973 | Guenther | |
| 3,957,055 A | 5/1976 | Linder | |
| 4,003,709 A | 1/1977 | Eaton | |
| 4,248,236 A * | 2/1981 | Linder | 604/100.01 |
| 4,691,701 A * | 9/1987 | Williams | 128/207.14 |
| 4,728,499 A * | 3/1988 | Fehder | 422/56 |
| 4,790,327 A | 12/1988 | Despotis | |
| 4,879,999 A * | 11/1989 | Leiman et al. | 128/207.14 |
| 4,928,687 A * | 5/1990 | Lampotang et al. | 128/207.14 |
| 4,938,211 A * | 7/1990 | Takahashi et al. | 128/204.26 |
| 4,945,918 A | 8/1990 | Abernathy | |
| 4,994,117 A | 2/1991 | Fehder | |

(Continued)

OTHER PUBLICATIONS

Gedeon et al., "A new colorimetric breath indicator (Colibri)", Anaesthesia 49:798-803 (1994).

(Continued)

*Primary Examiner*—Henry Bennett
*Assistant Examiner*—Andrew Bunin
(74) *Attorney, Agent, or Firm*—McKee, Voorhees & Sease, P.L.C.

(57) ABSTRACT

An improved endotracheal tube system and method of use is provided. The improved endotracheal tube system includes a standard endotracheal tube, a housing with a first tube that may be positioned within an endotracheal tube and a second tube adapted for attachment to a bag-valve mask. The housing has a $CO_2$ detector within it. The improved endotracheal tube system may also have a stylet positioned within the endotracheal tube and the housing. The stylet may have a handle attached to it for easy removal from the housing.

17 Claims, 7 Drawing Sheets

U.S. PATENT DOCUMENTS

| | | | | |
|---|---|---|---|---|
| 5,005,572 | A | 4/1991 | Raemer | |
| 5,058,577 | A * | 10/1991 | Six | 128/200.26 |
| 5,124,129 | A | 6/1992 | Riccitelli | |
| 5,156,159 | A | 10/1992 | Lampotang | |
| 5,166,075 | A | 11/1992 | Fehder | |
| 5,179,002 | A | 1/1993 | Fehder | |
| 5,197,464 | A * | 3/1993 | Babb et al. | 128/207.14 |
| 5,261,415 | A | 11/1993 | Dussault | |
| 5,279,289 | A | 1/1994 | Kirk | |
| 5,360,003 | A * | 11/1994 | Capistrano | 128/207.15 |
| 5,375,592 | A | 12/1994 | Kirk | |
| 5,456,249 | A | 10/1995 | Kirk | |
| 5,517,985 | A | 5/1996 | Kirk et al. | |
| 5,546,934 | A * | 8/1996 | Kaigler et al. | 128/205.13 |
| 5,679,884 | A | 10/1997 | Kirk | |
| 5,749,358 | A | 5/1998 | Good | |
| 5,789,660 | A | 8/1998 | Kofoed | |
| 6,257,236 | B1 * | 7/2001 | Dutkiewicz | 128/207.14 |
| 6,427,687 | B1 * | 8/2002 | Kirk | 128/203.11 |
| 6,584,974 | B1 | 7/2003 | Ratner | |
| 6,609,521 | B1 | 8/2003 | Belani et al. | |
| 6,874,504 | B1 * | 4/2005 | Raspallo | 128/207.14 |

OTHER PUBLICATIONS

FDA Pre-market notification, modifications to Class II devices, ICOR, Bromma, Sep. 5, 1995, 10 pages.

* cited by examiner

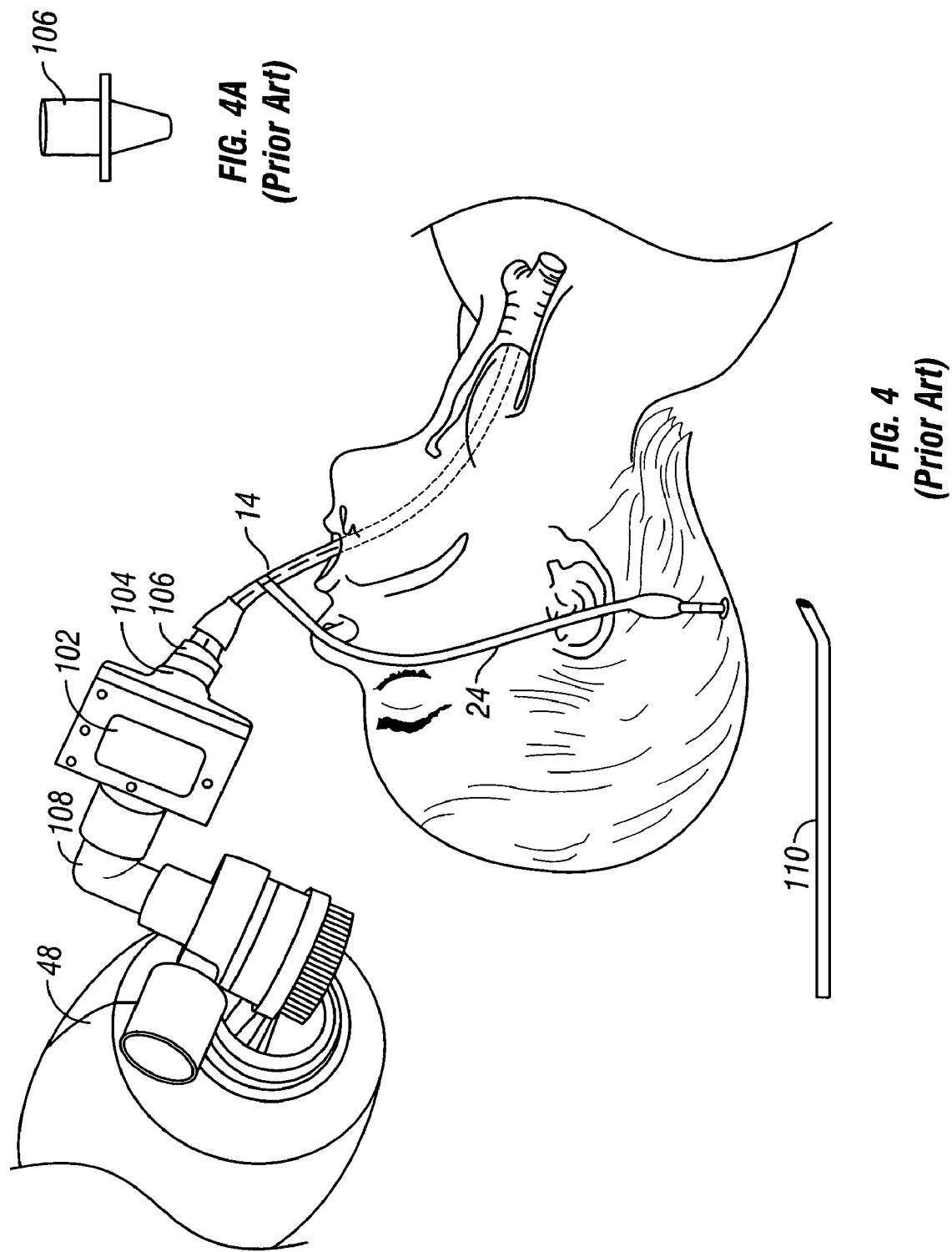

ENDOTRACHEAL TUBE SYSTEM AND METHOD OF USE

CROSS REFERENCE TO RELATED APPLICATIONS

This application is a Continuation-In-Part of U.S. patent application Ser. No. 10/829,033 filed on Apr. 21, 2004, the contents of which are hereby incorporated by reference in their entirety.

BACKGROUND OF THE INVENTION

The invention relates generally to the field of medical devices. Specifically, the invention relates to an endotracheal tube system that provides for proper placement of the endotracheal tube and for subsequence carbon dioxide detection.

A serious problem in the resuscitation of patients is the fast and efficient insertion of an endotracheal tube into a patient and then determining if the tube is in correct placement within the trachea. A medical professional responding to a patient who is not breathing has very little time to react because brain damage occurs after only four minutes without oxygen and brain death occurs at eight minutes without oxygen. Therefore, a need exists to provide the medical professional with an improved endotracheal tube system and method, of use which quickly and efficiently places the endotracheal tube within the patient and tests for proper placement.

Capnography is the term generally associated with monitoring carbon dioxide ($CO_2$) levels in an expired breath. Capnography specifically is the process of monitoring the concentration of exhaled carbon dioxide in order to assess the physiological status of patients receiving mechanical ventilation and to determine the adequacy of ventilation. It is difficult for the medical professional using a respirator to determine whether the patient is receiving an adequate flow of oxygen without some form of capnography. The medical professional must observe whether the lungs are filling with air or whether the stomach is gurgling because it is filling with air but without some form of capnography the medical professional is not assured whether the patient is receiving an adequate flow of oxygen. For example, the endotracheal tube may be inserted into the patient's esophagus instead of the trachea. Therefore, a need has arisen for an efficient and economical way of determining whether the patient being treated with a resuscitator is actually receiving oxygen.

Carbon dioxide detectors are well known in the prior art for use with an endotracheal tube. However, the prior art carbon dioxide detectors are both cumbersome and time consuming. Moreover, the prior art carbon dioxide detectors are not integral with the endotracheal tubes and therefore create problems when assembling prior to use upon a patient. Accordingly, an objective of the current invention is an improved endotracheal tube system which incorporates a $CO_2$ detector directly to an endotracheal tube, creating a single device.

There have been attempts in the prior art to design a resuscitator that integrates a carbon dioxide detector. An example of such a device is disclosed in U.S. Pat. No. 6,427,687 to Kirk. Unfortunately Kirk is both time consuming and cumbersome because it incorporates a carbon dioxide detector into the resuscitator. Therefore, a medical professional using Kirk must incorporate a disposable $CO_2$ detector upon the regulator thus requiring an additional step above merely inserting the endotracheal tube into the patient. A further example of a combination carbon dioxide detector and resuscitator is disclosed in U.S. Pat. No. 6,584,974 to Ratner. Ratner attaches the $CO_2$ detector directly to the resuscitator and has the same disadvantages as the Kirk patent. Accordingly, it is an objective of the present invention to incorporate the $CO_2$ detector in an adapter that may be placed between the endotracheal tube and a bag valve mask.

A further problem in the prior art is the inability to administer medications through the endotracheal tube without coming in direct contract with a carbon dioxide indicator. U.S. Pat. No. 4,879,999 to Leiman discloses a device for determining of proper endotracheal tube placement using a carbon dioxide indicator in open contact with the endotracheal tube; therefore, medication placed into the tube may easily contact the carbon dioxide indicator. Moreover, the Leiman patent may use support structure that makes the $CO_2$ housing cumbersome. Accordingly, it is a still further objective of the present invention to have a structure that prevents the carbon dioxide indicator from being contacted with medicine and to use the minimum of space outside the air channel of the housing to prevent a cumbersome structure.

An additional problem with the resuscitation of patients is the difficulty in placing the endotracheal tube within the trachea. This difficulty is overcome using a metal stylet placed within the endotracheal tube before insertion into the patient. The stylet provides rigidity to the endotracheal tube which provides the medical professional control of the flexible plastic tubing of the endotracheal tube. The stylet is not reusable and must be disposed after every use. The stylet is necessary in emergency situations to assist in manipulating an endotracheal tube through the glottic opening of the trachea that may be closed, partially collapsed, or blocked. The medical professional, because he or she may not know of the problems associated with the trachea, must use the stylet as a default for manipulating the endotracheal tube. Accordingly, an objective of the present invention is to incorporate a stylet into the endotracheal tube system.

Furthermore, prior art stylets commonly bend when pulling the stylet from the endotracheal tube and add to the risk of accidental removal of the tube from the trachea. Accordingly, an objective of the present invention is to incorporate an affixed handle to prevent bending and assist in the removing of the tube from the trachea. Additionally, the stylet and handle may be in close proximity to a carbon dioxide detector that needs to be protected from outside air. Accordingly, it is a still further objective to provide a handle that has the capability to block outside air from contacting the carbon dioxide detector.

A still further objective of the present invention is to minimize the amount of pieces and assembly required by medical personnel. Every additional piece that is not preassembled creates increased search time for the pieces, the possibility of dropping the pieces, and the concern for inadequate attachment of multiple parts of the assembled system. Therefore, a further objective of the present invention is to create an improved endotracheal tube system which has all pieces preassembled into a combination such that only a resuscitator or bag valve mask needs to be attached it.

A still further objective of the present invention is to minimize the amount of time for capnography and subsequent verification of endotracheal tube placement within the trachea as opposed to the esophagus. It is of the utmost concern that no time is wasted for attaching and assembling pieces to the endotracheal tube that could have been preassembled and packaged.

In addition, it is a still further objective of the present invention to produce an improved endotracheal tube system that is sold as a set as opposed to the individual pieces of an endotracheal tube, a $CO_2$ tube detector, and a stylet. The set can be sold for a reduced price as opposed to the individual prices set for individual pieces.

These and other objectives of the present invention will become apparent from the following description of the invention.

SUMMARY OF THE INVENTION

The improved endotracheal tube system utilizes an adapter that is placed between an endotracheal tube and the bag-valve mask. The adapter has a housing having a first tube for attachment to an endotracheal tube and a second tube for attachment to a bag-valve mask. The adapter has a carbon dioxide indicator within the housing that is in gaseous communication with the endotracheal tube but isolated from the outside atmosphere. The adaptor has a fin to direct air from the second tube unidirectionally to the carbon dioxide indicator.

The improved endotracheal tube system has an endotracheal tube, a housing containing a first tube attached to the endotracheal tube and a second tube for attachment to a bag-valve mask. The system also having a stylet placed within the endotracheal tube and the housing to provide temporary rigidity to the endotracheal tube. The improved endotracheal tube system may also have a carbon dioxide indicator within the housing and fins that project into the first tube to impede airflow from the endotracheal tube and direct the airflow to the carbon dioxide indicator. Additionally, the system may have a handle attached to the stylet that facilitates removal of a stylet from the endotracheal tube and the adapter but with handle having seals upon it which prevent the outside atmosphere air from interacting with the carbon dioxide indicator.

In the method of the invention, an improved endotracheal tube system is supplied to the medical professional. The medical professional positions an endotracheal tube of the system into a patient. The medical professional will then remove the stylet from the endotracheal tube and a housing. The medical professional then places a bag-valve mask upon the housing and ventilates the patient. One ventilation cycle effectively creates a color change in the carbon dioxide indicator of the system. If the carbon dioxide indicator changes color, the endotracheal tube is correctly placed within the trachea. When the endotracheal tube is not properly placed, no color change will be apparent. If incorrectly placed, vomit or other stomach contents may enter the endotracheal tube and, consequently, the endotracheal tube must be discarded. Medicine may be administered to the patient through the housing because fins protect the carbon dioxide indicator.

BRIEF DESCRIPTION OF THE DRAWINGS

FIG. 4 is a picture of the prior art endotracheal tube system with a bag-valve mask attached to it.

FIG. 4A is a front view of the adapter of FIG. 4.

DETAILED DESCRIPTION OF THE PREFERRED EMBODIMENT

Figure 1:
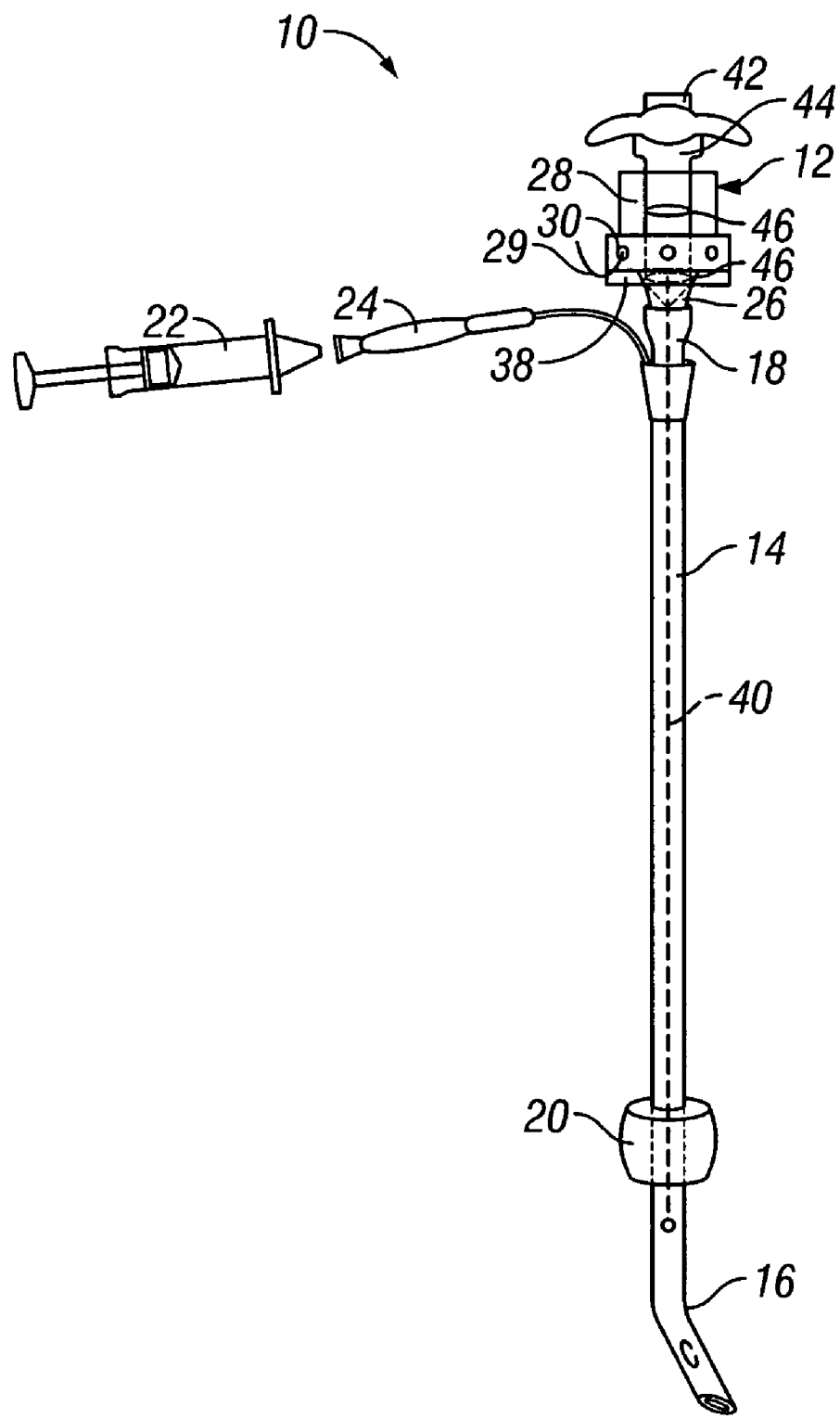
FIG. 1 is a front view of the improved endotracheal tube system of the present invention.

Referring now to FIG. 1, the improved endotracheal tube system is generally designated by the reference numeral 10. The system has an adaptor or interconnection 12 that attaches to a standard endotracheal tube 14.

The endotracheal tube 14 has a distal end 16 that is positioned within a patient's trachea. The endotracheal tube 14 also has a proximal end 18 in which the adapter 12 is placed. A standard endotracheal tube has a balloon 20 that is inflated once the endotracheal tube 14 is positioned in the patient. The balloon 20 prevents accidental withdrawal of the endotracheal tube from the trachea and specifically movement past the patient's vocal chords. The balloon 20 is inflated by placing a syringe 22 into the balloon inflating apparatus 24. The standard endotracheal tube may also have medication ports, suction ports, and other ports as disclosed in the prior art.

The housing 12 has a first tube 26 that fits into the proximal end 18 of the endotracheal tube 14. The first tube 26 may be tapered for insertion into various sizes of endotracheal tube 18. Alternatively, the first tube 26 may be connected to the endotracheal tube to form an assembly. The first tube may be various sizes depending upon the size of the endotracheal tube 18 used. Endotracheal tubes 18 may vary depending on the size and age of the patient. The adaptor has a second tube 28 for attachment to a bag-valve mask. The second tube 28 has an outer diameter that may range between 12 millimeters (mm) to 20 mm and preferably has an outside diameter of 14 mm with an inner diameter of 13 mm. The cylinder is preferably 16 mm to 24 mm in length with a preferred length of 18 mm.

Figure 2:
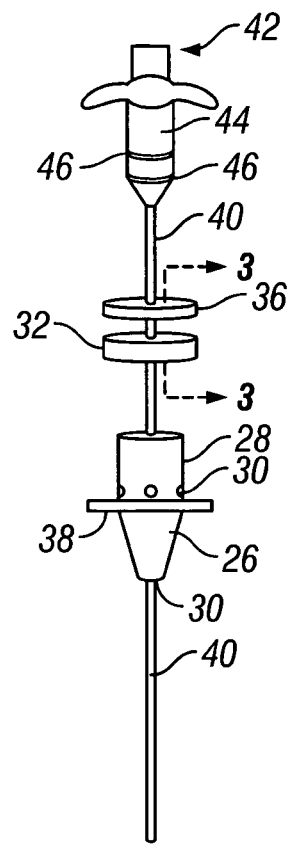
FIG. 2 is an exploded view of the adapter with a carbon dioxide detector and a stylet having a handle attached to it.
Figure 2A:
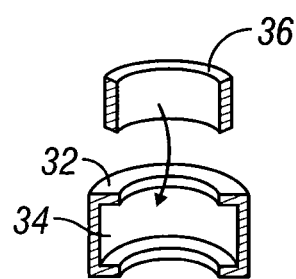
FIG. 2A is a sectional view along line 2A—2A of FIG. 2.
Figure 2B:
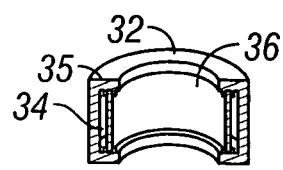
FIG. 2B is an alternate embodiment of the adapter having the carbon dioxide detector held in tracks.

As seen in FIG. 2, on the base of the second tube 28 are six holes equally spaced around the circumference of the second tube 28. The holes 30 measure approximately 3 mm in diameter. As seen in FIG. 2A, a ring 32 with a C-shaped cross section defining a ring chamber 34 is adapted to be placed over the second tube 28. Inside the ring chamber 34 is placed a carbon dioxide indicator 36. Litmus paper is chemically treated telemetric indicator paper that may be used to detect carbon dioxide. The carbon dioxide detector 36 goes into ring 32. The ring 32 may then be slid over the second tube 28 and positioned against flange 38. The ring 32 is then secured in place. The ring may be secured using adhesive between the interface of the ring 32 and second tube 28 and the ring 32 and flange 38. As seen in FIG. 2B, the carbon dioxide detector may be held in tracks 35 of the ring 34.

Figure 3:
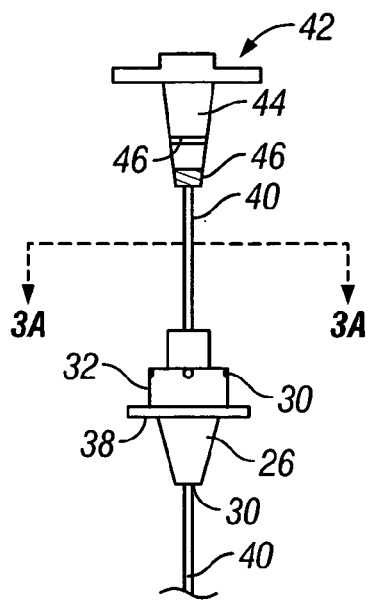
FIG. 3 is an exploded view of an alternate embodiment of the improved endotracheal tube system.
Figure 3A:
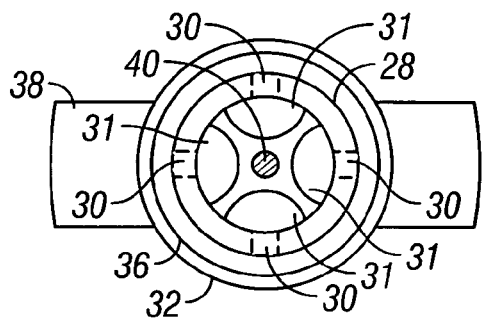
FIG. 3A is a sectional view along 3A—3A of FIG. 3.
Figure 3B:
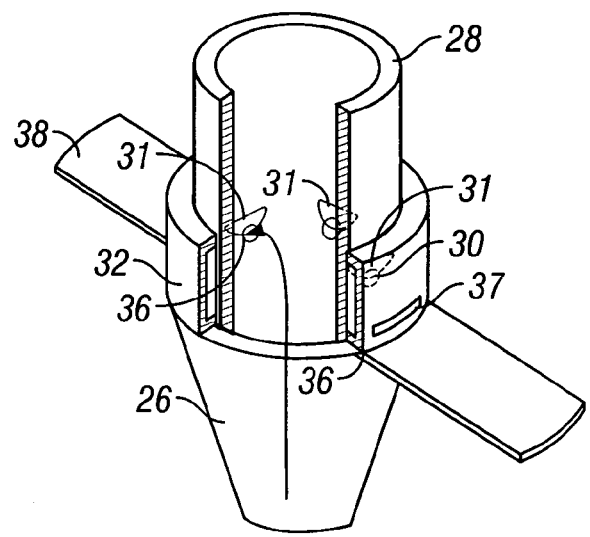
FIG. 3B is a partially cut away housing of FIG. 3.

As seen in FIG. 3, an alternate embodiment of the adaptor 12 is illustrated. Similar to the adaptor 12 of FIGS. 1 and 2, the alternate embodiment adaptor 12 has a first tube 26 and a second tube 28. On the base of the second tube 28 are four holes equally spaced around the circumference. These holes measure approximately 4 mm in diameter. Immediately above the holes are fins 31. Fins 31 are more clearly seen in FIGS. 3A and 3B. As seen in FIG. 3D, the fins act to direct air coming up the endotracheal tube 14 into hole 30 so that it may influence the carbon dioxide indicator 36. The fins 31 project into the second tube to impede airflow from the endotracheal tube 14 and direct the airflow to the carbon dioxide indicator. The air directed away from the fin 31 moves in a unidirectional direction to the carbon dioxide indicator 36 to facilitate a color change. The fins 31 also facilitate the administering of medicine through the adaptor without damaging the carbon dioxide indicator 36. A slit 37 may be in ring 32 to help promote unidirectional flow of air past the $CO_2$ indicator 36. Medicine coming from outside the endotracheal tube 14 is directed by the fins or other unidirectional airflow enabling structure, away from holes 30, and down into the endotracheal tube 14 using fins 31, and is unlikely to enter into holes 30 to damage the carbon dioxide indicator 36.

Although the fins 31 are illustrated as causing unidirectional airflow other structures may be provided for unidirectional airflow. For example, a one-way valve may be used to direct air from the ET tube 18 across the $CO_2$ indicator 36 but not permit air from the bag-valve mask 48. Additionally, there could be multiple variations of a unidirectional airflow system made in the ET tube adaptor such as a directional ring or cone. Furthermore, the number of fins 31 may be varied.

A stylet 40 is placed within the endotracheal tube 14 and the housing 12. A stylet provides rigidity to the endotracheal tube when being placed within a user's trachea. The stylet is attached to handle 42. The handle 42 has a plug 44 with seals 46 upon it. The plug 44 and seals 46 press upon the inner chamber of the housing 12 so that air cannot come in contact with the $CO_2$ detecting paper 36. FIGS. 1 and 2 illustrates one seal 46 above the holes 30 and a second seal 46 below the holes 30. FIG. 3 has a gasket type seal above the holes 30 and a plug type seal below the holes 30. The position of the seals 46 is relevant because the distal end 16 of the endotracheal tube 14 is not sealed.

The present invention may be embodied as an assembly including an endotracheal tube 14, a housing 12, and a stylet. The prior art has never addressed this assembly combination which is of a necessary benefit to emergency medical professions. Different types of housings including $CO_2$ detectors may be substituted such as those by Leiman, U.S. Pat. No. 4,879,999, and Riccitelli, U.S. Pat. No. 5,124,129.

As seen in FIG. 4, the prior art used a cumbersome $CO_2$ detector having one end 104 that attaches to an endotracheal tube adapter 106. As seen in FIG. 4A, an endotracheal tube adapter 106 used in the prior art is of the same general size as the housing 12 of the present invention but does not utilize any carbon dioxide indictor that is in gaseous communication with the endotracheal tube and isolated from the outside air or atmosphere. The $CO_2$ detector 102 in the prior art also has a second end 108 that is adapted to receive a bag-valve mask 48.

The prior art as seen in FIG. 4 has four discreet pieces. The first two pieces being the endotracheal tube 14 with a standard adapter 106. These two pieces are typically supplied together and are sealed in a separate package. The third piece is the $CO_2$ detector 102. The $CO_2$ detector 102 comes in a separate bag. The fourth piece is the stylet 110 which is a separate piece removed from the endotracheal tube 14 and adapter 106 before placing the $CO_2$ detector 102 upon the adapter 106. The bag-valve mask 48 is reusable and therefore not considered as an additional piece. The following table illustrates the number of steps and times associated with using the prior art color $CO_2$ detector 102.

TABLE 1

Prior art $CO_2$ Detector Steps and Times

| STEP | PROCEDURE | SECONDS |
|---|---|---|
| Step 1 | Find endotracheal tube | 5–10 |
| Step 2 | Open endotracheal tube bag and remove from bag | 1–2 |
| Step 3 | Find stylet | 5–10 |
| Step 4 | Open stylet bag | 1–2 |
| Step 5 | Insert the stylet into endotracheal tube | 5–10 |
| Step 6 | Find $CO_2$ detector | 5–10 |
| Step 7 | Open $CO_2$ detector bag | 1–2 |
| Step 8 | Utilize Larynengscope, find trachea, insert endotracheal tube | 15–30 |
| Step 9 | Fully inflate balloon | 4–8 |
| Step 10 | Remove stylet | 1–2 |
| Step 11 | Attach $CO_2$ detector | 1–2 |
| Step 12 | Attach bag to $CO_2$ detector | 2–4 |
| Step 13 | Ventilate | 10–15 |
| Step 14 | Check for color change | 1 |
| Step 15 | Remove bag from $CO_2$ detector | 1–2 |
| Step 16 | Remove $CO_2$ detector from endotracheal tube | 5–15 |
| Step 17 | Replace ventilator onto endotracheal tube to ventilate | 2–4 |

As seen in the above table, the best case scenario for emergency medical personnel to insert an endotracheal tube into a person is 64 seconds. The worst case scenario takes much more time. A medical professional is under an extreme amount of stress knowing that in four minutes a person will encounter brain damage and that in eight minutes a person will encounter brain death. Therefore, the medical professional will be experiencing both adrenaline and anxiety. In addition, the medical professional may have problems and find the trachea obscured by the tongue or fatty deposits in the mouth. In addition, the worst case scenario may take much more time because the color change did not indicate that the endotracheal tube was in the trachea and then the medical professional must go back and repeat the steps beginning at Step 1. In addition, the medical professional may accidentally withdraw the adapter 106 from the endotracheal tube 14 when removing the $CO_2$ detector 102 and then the person will again have to repeat Step 1.

In summary, the best case scenario for the prior art method of detecting $CO_2$ may range between 64 to 126 second. The worst case scenario may range much longer than two minutes and creep dangerously close to the four minute mark for brain damage and the eight minute mark for brain death. Obviously, with the medical professional also having to encounter delaying issues such as being transported to an accident site on the highway, every second matters.

Figure 5:
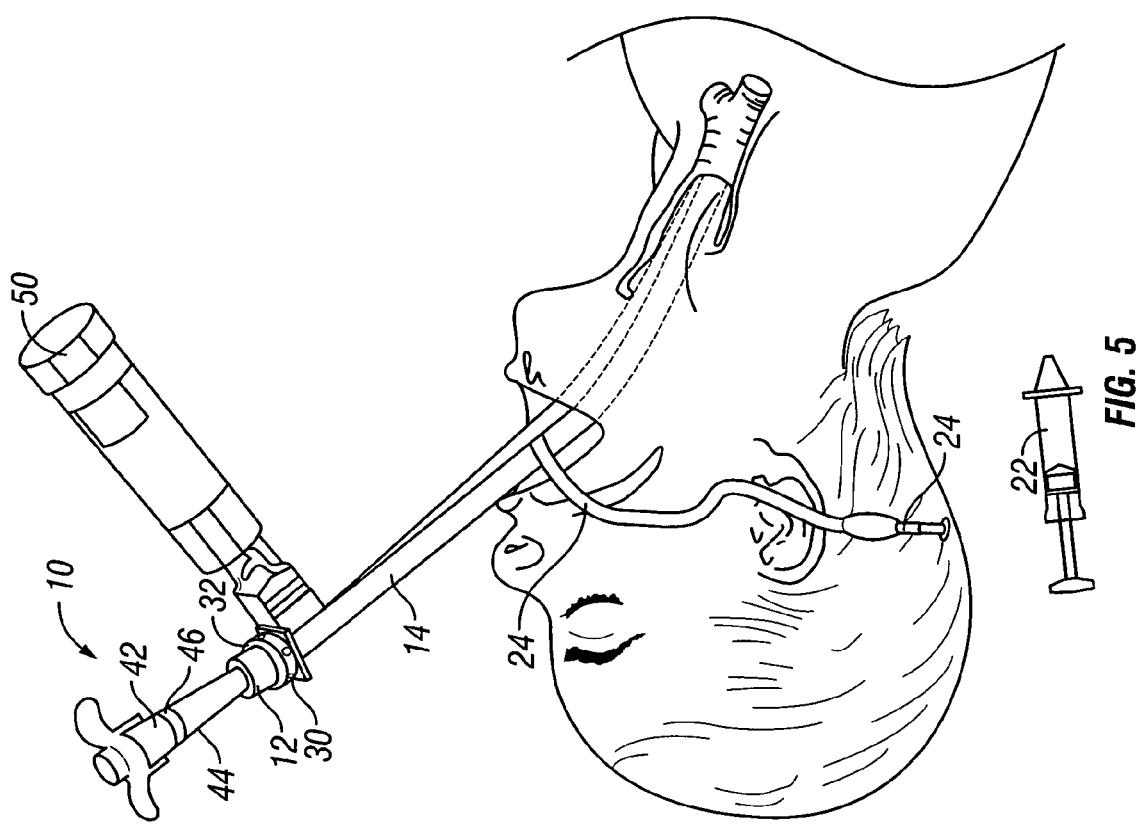
FIG. 5 is the improved endotracheal tube system of the present invention being inserted into a patient.
Figure 6:
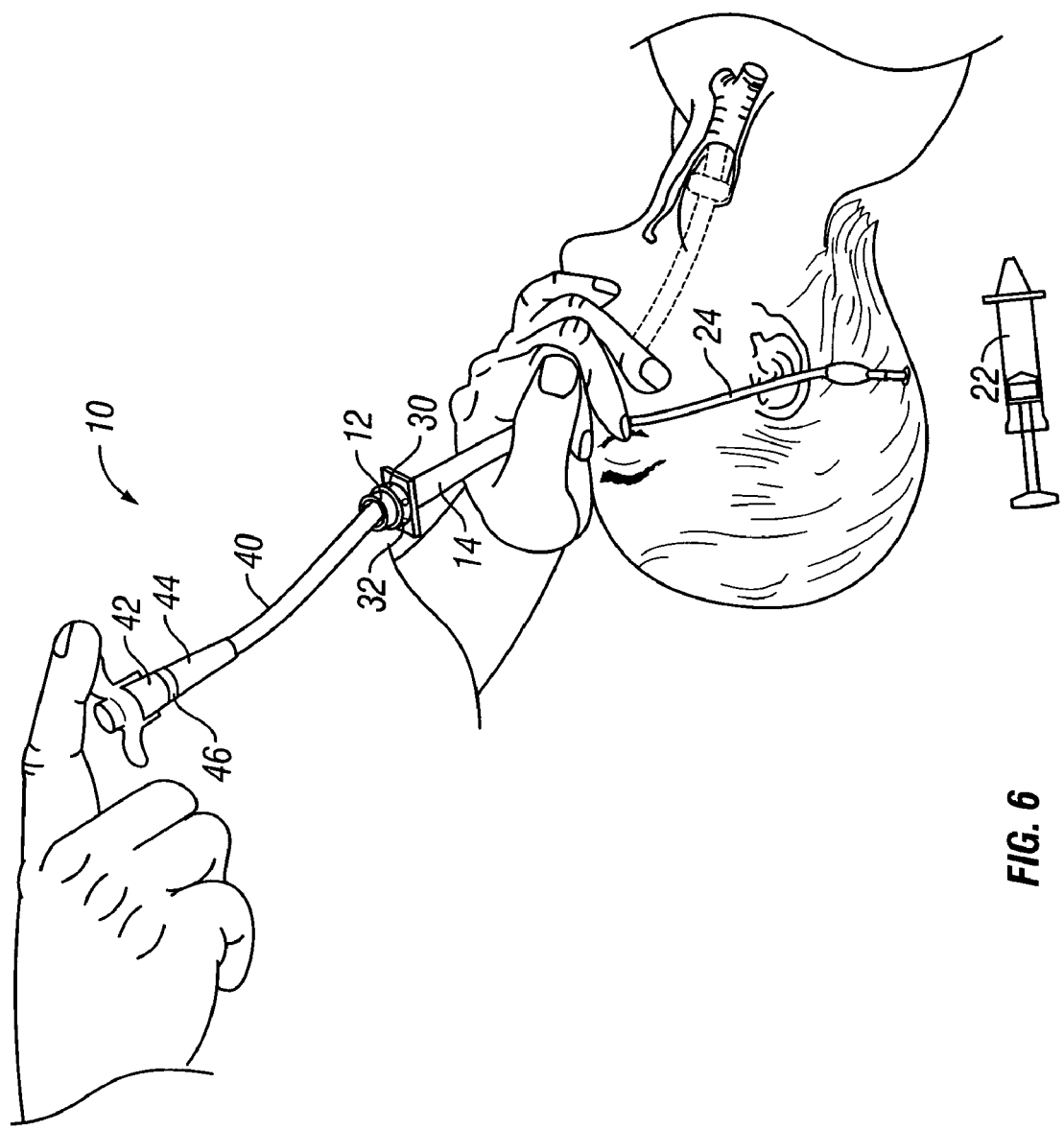
FIG. 6 is the improved endotracheal tube system of the present invention with the handle and stylet removed from the endotracheal tube.
Figure 7:
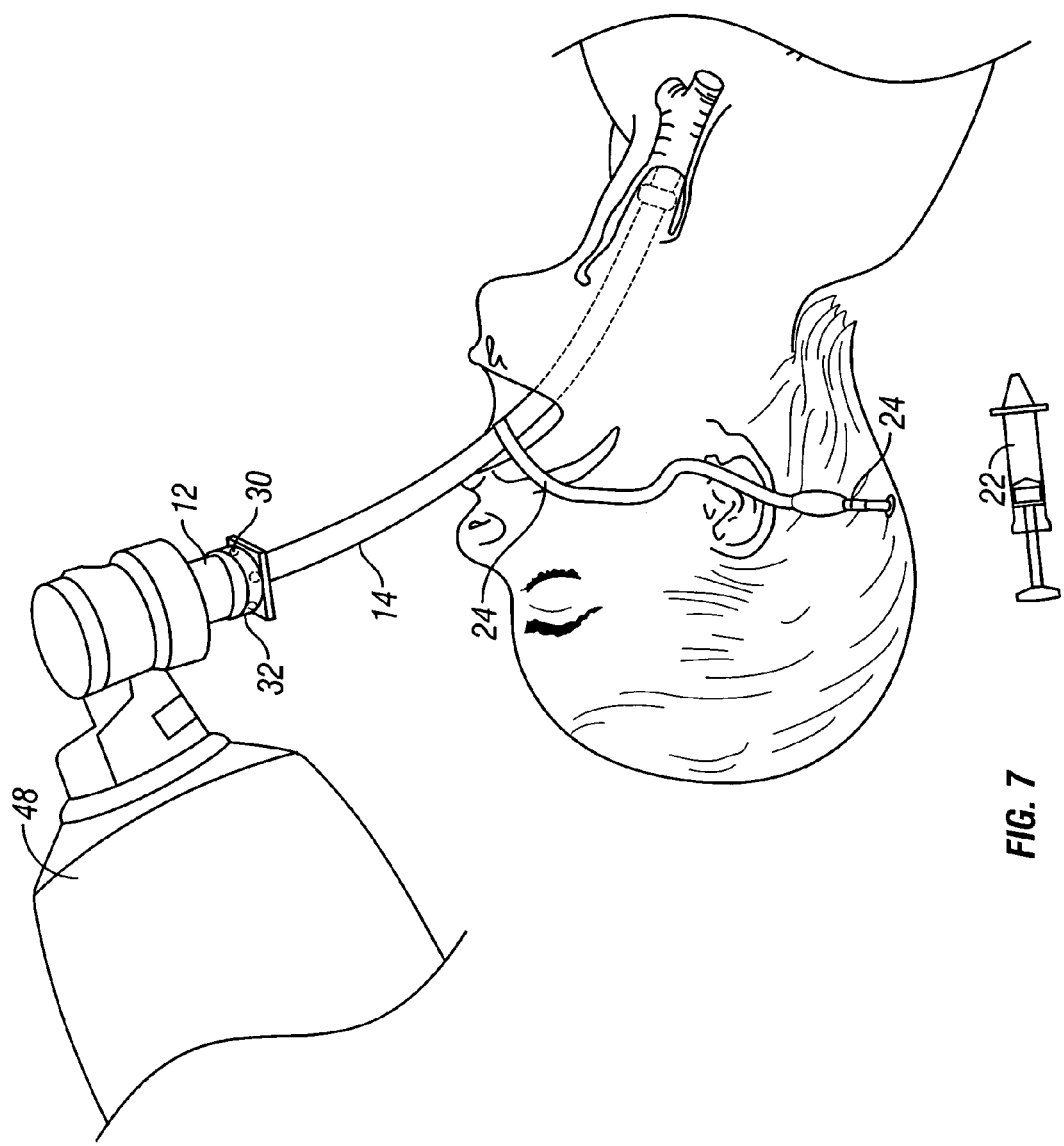
FIG. 7 is the improved endotracheal tube system of the present invention with the bag-valve mask attached to the adapter.

The present invention as seen in FIGS. 5–7 reduces the amount of steps and time. These reductions decreases the best case scenario time for inserting the endotracheal tube and limits the possibility for error encountered.

TABLE 2

The Present Invention's Steps for Inserting an Endotracheal Tube and Ventilating.

| STEP | PROCEDURE | SECONDS |
|---|---|---|
| Step 1 | Find endotracheal tube system | 5–10 |
| Step 2 | Open endotracheal tube system bag | 1–2 |
| Step 3 | Insert Laryngoscope, find trachea, insert endotracheal tube | 15–30 |
| Step 4 | Fully inflate balloon | 4–8 |

TABLE 2-continued

The Present Invention's Steps for Inserting an
Endotracheal Tube and Ventilating.

| STEP | PROCEDURE | SECONDS |
|---|---|---|
| Step 5 | Remove stylet plug | 1–2 |
| Step 6 | Attach bag to adapter with $CO_2$ detector | 2–4 |
| Step 7 | Ventilate | 5 |
| Step 8 | Check for Color Change | 1 |

As seen in the above table, the best case scenario results in a process which takes between 34 to 62 seconds and reduces the amount of steps from 17 to 8. In addition, the ventilation step is 5 seconds as opposed to 10–15 seconds because this design does not require a filter pad between the litmus paper and the inner surface of the second tube 28 because of the constantly sealed nature of the $CO_2$ detector using the handle 42. The prior art requires 10–15 seconds because it may require two to three ventilations of the bag as opposed to only one ventilation of the present invention. The present invention also has reduced time because it does not require needless opening of multiple bags but only one bag having the combination within it. The present invention also has a reduced amount of time in a worse case scenario as the $CO_2$ detector will not be accidentally removed by having the bag valve removed to remove the $CO_2$ detector.

As a summary of FIGS. 5–7, the medical provider first inserts the improved endotracheal tube system into a patient using a Laryngoscope 50. As seen in FIG. 6, the medical provider then inflates the balloon 20 using a syringe 22 attached to inflating apparatus 24. The user can then withdraw the handle 42 from the adapter 12 thus pulling the stylet 40 from the endotracheal tube in the adapter. As in FIG. 7, the user then attaches the bag-valve mask or ventilator 48 and compresses the bag to press air into the patient's lungs. The medical provider then permits the bag-valve mask to pull gas from the patient and if it is properly placed on the trachea, it will pull $CO_2$ rich gas from the user's lungs and direct it to the $CO_2$ detector and the housing 12. If there is no color change, the medical provider will remove the endotracheal tube 14 from the patient and replace with a fresh tube. If the endotracheal tube is in the trachea, the medical provider will continue to respirate the patient.

The invention has been shown and described above with the preferred embodiments, and it is to be understood that many modifications, substitutions, and additions may be made which are within the intended spirit and scope of the invention. From the foregoing, it can be seen that the present invention accomplishes at least all of its stated objectives.

What is claimed is:

1. An interconnection to be placed between an endotracheal tube and bag-valve mask, the interconnection comprising:
   a first tube for attachment to an endotracheal tube and a second tube for attachment to a bag-valve mask;
   a carbon dioxide indicator on the second tube, in gaseous communication with the endotracheal tube
   a housing over the carbon dioxide indicator to isolate the indicator from outside air;
   at least one inlet orifice in the second tube,
   a carbon dioxide indicator covering the orifice
   a structure for directing air from the endotracheal tube unidirectionally through the orifice to the carbon dioxide indicator.

2. The interconnection of claim 1 wherein four orifices are spaced around the second tube and the carbon dioxide indicator surrounds the second tube over the orifices and the structure is a fin above each orifice.

3. The interconnection of claim 2 wherein the orifice is approximately 4 mm in diameter.

4. The interconnection of claim 1 further comprising an outlet orifice in the housing to promote unidirectional air flow.

5. The interconnection of claim 4 wherein the outlet orifice exhausts to the outside air.

6. The interconnection of claim 5 wherein the carbon dioxide indicator is a chemically treated colorimetric indicator paper.

7. The interconnection of claim 1 wherein the housing is a clear ring.

8. The interconnection of claim 7 wherein the clear ring has a C-shaped cross section defining a channel for receiving the carbon dioxide indicator.

9. A combination comprising:
   an endotracheal tube;
   an adaptor with a first tube attached to the endotracheal tube and a second tube for attachment to a bag-valve mask;
   at least one orifice in the second tube,
   a carbon dioxide indicator covering the orifice;
   a fin that projects into the second tube to direct the airflow to the carbon dioxide indicator;
   a stylet extending through the endotracheal tube and through the adapter to provide temporary rigidity to the endotracheal tube.

10. The combination of claim 9 further comprising a handle attached to the stylet to facilitate removal of the stylet from the endotracheal tube and the adapter.

11. The combination of claim 10 wherein the handle interfaces the second tube to form a seal.

12. The combination of claim 10 wherein the handle interfaces with the first tube and the second tube to form a seal.

13. The combination of claim 9 wherein the airflow directed from the fin is unidirectional across the carbon dioxide indicator.

14. A method of placing an endotracheal tube within a patient and testing for placement within the patient's trachea, the method comprising:
   providing a bag-valve mask an endotracheal tube, an adaptor attached to the endotracheal tube and an orifice, a carbon dioxide indicator covering the orifice and a fin adjacent the orifice, and a stylet within the endotracheal tube and the adaptor;
   placing the endotracheal tube within the patient;
   removing the stylet from the endotracheal tube and the housing;
   placing the bag-valve mask upon the housing and ventilating the patient;
   directing air with the fin unidirectionally through the orifice to the carbon dioxide indicator, end
   determining proper placement within the patients trachea by observing the carbon dioxide indicator.

15. The method of claim 14 further comprising providing hermetically sealed packaging for an assembly of the endotracheal tube, the housing, and the stylet;
   removing the assembly from the packaging.

16. The method of claim 14 further comprising:
   providing a handle attached to the stylet and interfaced with the housing to form an air-tight seal;
   gripping the endotracheal tube with one hand and pulling the handle to remove the stylet.

17. The method of claim 14 further comprising the step engaging the bag-valve mask for one ventilation cycle.

* * * * *